US008309076B2

(12) United States Patent
Kang et al.

(10) Patent No.: US 8,309,076 B2
(45) Date of Patent: Nov. 13, 2012

(54) LACTIC ACID BACTERIA ISOLATED FROM MOTHER'S MILK WITH PROBIOTIC ACTIVITY AND INHIBITORY ACTIVITY AGAINST BODY WEIGHT AUGMENTATION

(75) Inventors: Ji Hee Kang, Busan (KR); Byeung Il You, Daejeon (KR); Sung Il Yun, Chungcheongnam-do (KR); Han Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 430 days.

(21) Appl. No.: 12/376,368

(22) PCT Filed: May 14, 2007

(86) PCT No.: PCT/KR2007/002363
§ 371 (c)(1),
(2), (4) Date: Mar. 17, 2010

(87) PCT Pub. No.: WO2008/016214
PCT Pub. Date: Feb. 7, 2008

(65) Prior Publication Data
US 2010/0203025 A1 Aug. 12, 2010

(30) Foreign Application Priority Data
Aug. 4, 2006 (KR) .................. 10-2006-0073722

(51) Int. Cl.
*A61K 35/74* (2006.01)
*C12N 1/20* (2006.01)
(52) U.S. Cl. ............... 424/93.45; 424/184.1; 435/252.9
(58) Field of Classification Search .................. None
See application file for complete search history.

(56) References Cited

U.S. PATENT DOCUMENTS

| 6,808,703 | B2 | 10/2004 | Park et al. |
| 6,942,857 | B2 | 9/2005 | Song et al. |
| 7,001,756 | B1 | 2/2006 | Hsu et al. |
| 7,807,440 | B2 * | 10/2010 | Molin et al. ............... 435/252.1 |
| 2004/0115179 | A1 | 6/2004 | Liu et al. |

FOREIGN PATENT DOCUMENTS

| JP | 2005-080636 A | 3/2005 |
| WO | 2004/003235 A3 | 1/2004 |

OTHER PUBLICATIONS

Pavlova et al 2002, J. Appl. Microbiol. 92 (3), 451-459.*
Supplementary European Search Report issued in EP Appln. No. 07 74 6512, dated Aug. 17, 2010, 2 pages.
A. C. Majhenic, et al.: "DNA analysis of the genes encoding acidocin LF221 A and acidocin LF221 B, two bacteriocins produced by *Lactobacillus gasseri* LF221," Appl. Microbiol. Biotechnol., vol. 63, Sep. 18, 2003, pp. 705-714.
NCBI GenBank Accession No. AY297947: "*Lactobacillus gasseri* putative complement factor, acidocin LF221B, and putative immunity protein genes, complete cds; and unknown genes," Nov. 4, 2005, 2 pages.
Y. Kawai et al.: "Primary Amino Acid and DNA Sequences of Gassericin T, a Lactacin F-Family Bacteriocin Produced by *Lactobacillus gasseri* SBT2055," in Biosci. biotechnol. Biochem, vol. 64(10), Jun. 6, 2000, pp. 2201-2208.
NCBI GenBank Accession No. AB029612: "*Lactobacillus gasseri* gassericin T gene region (ORF1, ORF2, ORF3, gatA, gatX, ORF6), complete cds," Oct. 27, 2000, 3 pages.
Majhenic, A.G. et al., DNA analysis of the genes encoding acidocin LF221 A and acidocin LF221 B, two bacteriocins produced by *Lactobacillus gasseri* LF221, Appl. Microbiol. Biotechnol., vol. 63, pp. 705-714. (2004).

* cited by examiner

*Primary Examiner* — Padma Baskar
(74) *Attorney, Agent, or Firm* — Rothwell, Figg, Ernst & Manbeck, P.C.

(57) ABSTRACT

The present invention relates to a lactic acid bacterium isolated from human mother's milk, more precisely a *Lactobacillus gasseri* BNR17 strain that is isolated from Korean mother's milk and has excellent probiotic activity including acid resistance, bile acid resistance and antimicrobial activity and weight gaining inhibitory effect as well. Again, the *Lactobacillus gasseri* BNR17 of the present invention has excellent acid resistance, bile acid resistance, enteric absorption activity and antimicrobial activity against pathogenic microorganisms, in addition to the weight gaining inhibitory effect by synthesizing indigestible polysaccharides from monosaccharides included in food taken and releasing the synthesized polysaccharides out of the body. Therefore, the strain of the invention, owing to such beneficiary effects, can be effectively used not only for the production of fermented milk, other fermented food products and animal feeds but also for the production of live cell products and food additives for preventing weight gaining.

8 Claims, 4 Drawing Sheets

[Fig. 1]

| | |
|---|---|
| BNR17 | GCTGACTCCTATAAAGGTTATCCCACCGGCTTTGGGTGTTACAGACTCTCATGGTGTGAC 88 |
| AF243156 | GCTGACTCCTATAAAGGTTATCCCACCGGCTTTGGGTGTTACAGACTCTCATGGTGTGAC 120 |
| BNR17 | GGGCGGTGTGTACAAGGCCCGGGAACGTATTCACCGCGGCGTGCTGATCCGCGATTACTA 148 |
| AF243156 | GGGCGGTGTGTACAAGGCCCGGGAACGTATTCACCGCGGCGTGCTGATCCGCGATTACTA 180 |
| BNR17 | GCGATTCCAGCTTCGTGTAGGCGAGTTGCAGCCTACAGTCCGAACTGAGAACGGCTTTCA 208 |
| AF243156 | GCGATTCCAGCTTCGTGTAGGCGAGTTGCAGCCTACAGTCCGAACTGAGAACGGCTTTCA 240 |
| BNR17 | NAGATCCGCTTGCCTTCGCAGGTTCGCTTCTCGTTGTACCGTCCATTGTAGCACGTGTGT 268 |
| AF243156 | GAGATCCGCTTGCCTTCGCAGGTTCGCTTCTCGTTGTACCGTCCATTGTAGCACGTGTGT 300 |
| BNR17 | AGCCCAGGTCATAAGGGGCATGATGACTTGACGTCATCCCCACCTTCCTCCGGTTTGTCA 328 |
| AF243156 | AGCCCAGGTCATAAGGGGCATGATGACTTGACGTCATCCCCACCTTCCTCCGGTTTGTCA 360 |
| BNR17 | CCGGCAGTCTCATTAGAGTGCCCAACTTAATGATGGCAACTAATGACAAGGGTTGCGCTC 388 |
| AF243156 | CCGGCAGTCTCATTAGAGTGCCCAACTTAATGATGGCAACTAATGACAAGGGTTGCGCTC 420 |
| BNR17 | GTTGCGGGACTTAACCCAACATCTCACGACACGAGCTGACGACAGCCATGCACCACCTGT 448 |
| AF243156 | GTTGCGGGACTTAACCCAACATCTCACGACACGAGCTGACGACAGCCATGCACCACCTGT 480 |
| BNR17 | CTCAGCGTCCCCGAAGGGAACTCCTAATCTCTTAGGTTTGCACTGGATGTCAAGACCTGG 508 |
| AF243156 | CTCAGCGTCCCCGAAGGGAACTCCTAATCTCTTAGGTTTGCACTGGATGTCAAGACCTGG 540 |
| BNR17 | TAAGGTTCTTCGCGTTGCTTCGAATTAAACCACATGCTCCACCGCTTGTGCGGGCCCCCG 568 |
| AF243156 | TAAGGTTCTTCGCGTTGCTTCGAATTAAACCACATGCTCCACCGCTTGTGCGGGCCCCCG 600 |
| BNR17 | TCAATTCCTTTGAGTTTCAACCTTGCGGTCGTACTCCCCAGGCGGAGTGCTTAATGCGTT 628 |
| AF243156 | TCAATTCCTTTGAGTTTCAACCTTGCGGTCGTACTCCCCAGGCGGAGTGCTTAATGCGTT 660 |
| BNR17 | AGCTGCAGCACTGAGAGGCGGAAACCTCCCAACACTTAGCACTCATCGTTTACGGCATGG 688 |
| AF243156 | AGCTGCAGCACTGAGAGGCGGAAACCTCCCAACACTTAGCACTCATCGTTTACGGCATGG 720 |
| BNR17 | ACTACCAGGGTATCTAATCCTGTTCGCTACCCATGCTTTCGAGCCTCAGCGTCAGTTGCA 748 |
| AF243156 | ACTACCAGGGTATCTAATCCTGTTCGCTACCCATGCTTTCGAGCCTCAGCGTCAGTTGCA 780 |
| BNR17 | GACCAGAGAGCCGCCTTCGCCACTGGTGTTCTTCCATATATCTACGCATTCCACCGCTAC 808 |
| AF243156 | GACCAGAGAGCCGCCTTCGCCACTGGTGTTCTTCCATATATCTACGCATTCCACCGCTAC 840 |
| BNR17 | ACATGGAGTTCCACTCTCCTCTTCTGCACTCAAGTTCAACAGTTTCTGATGCAATTCTCC 868 |
| AF243156 | ACATGGAGTTCCACTCTCCTCTTCTGCACTCAAGTTCAACAGTTTCTGATGCAATTCTCC 900 |

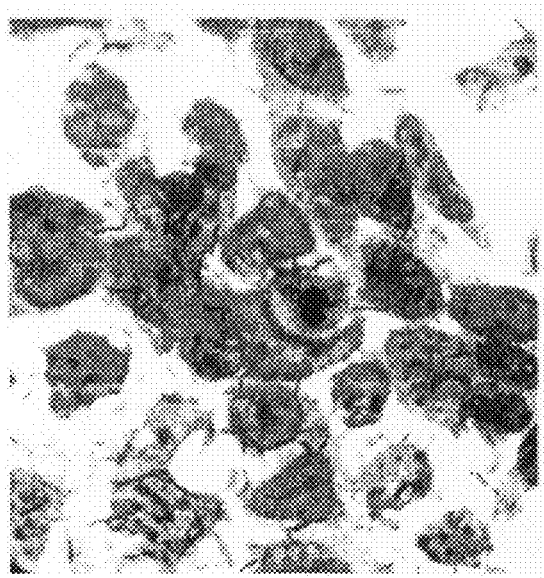
[Fig. 2]
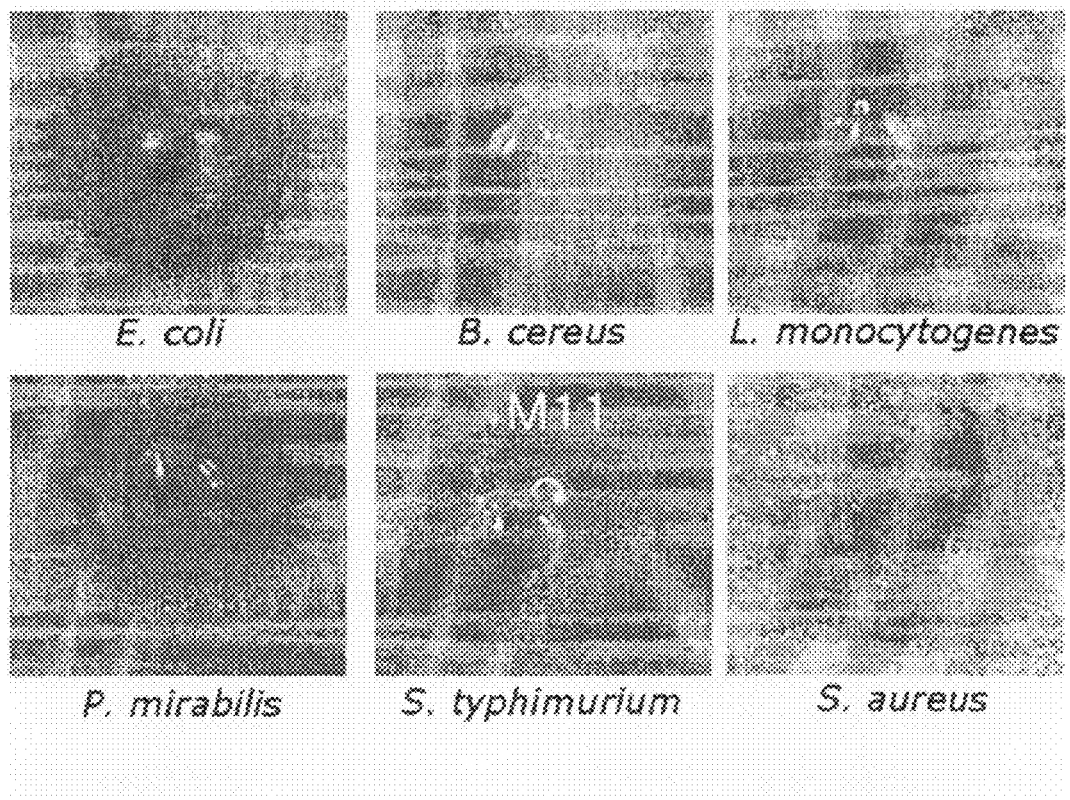
[Fig. 3]

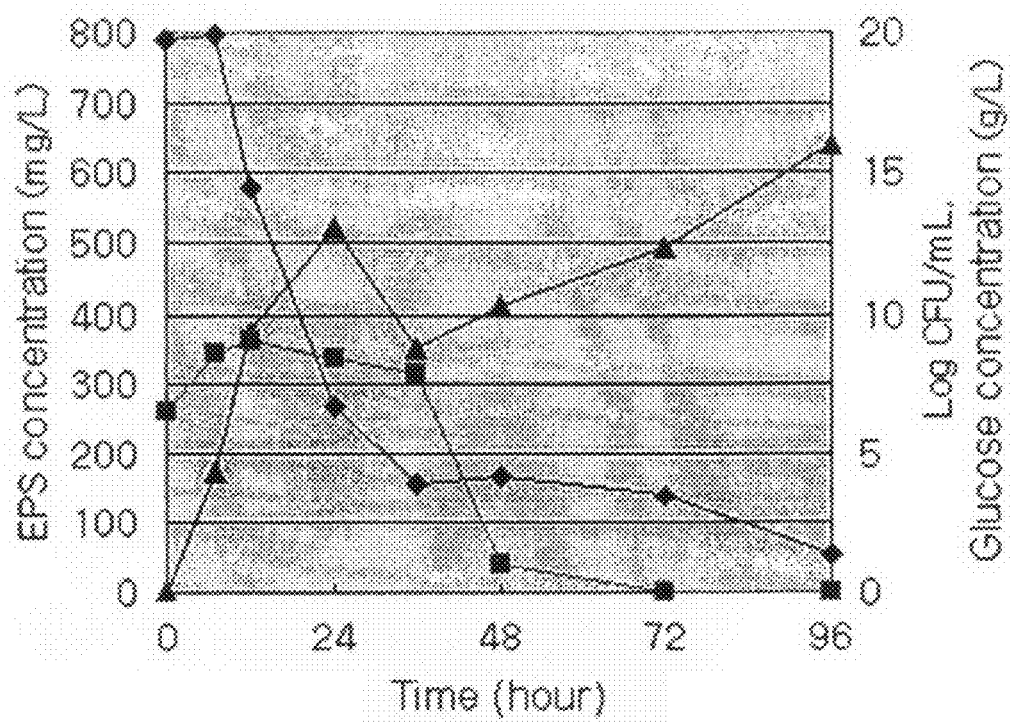
[Fig. 4]
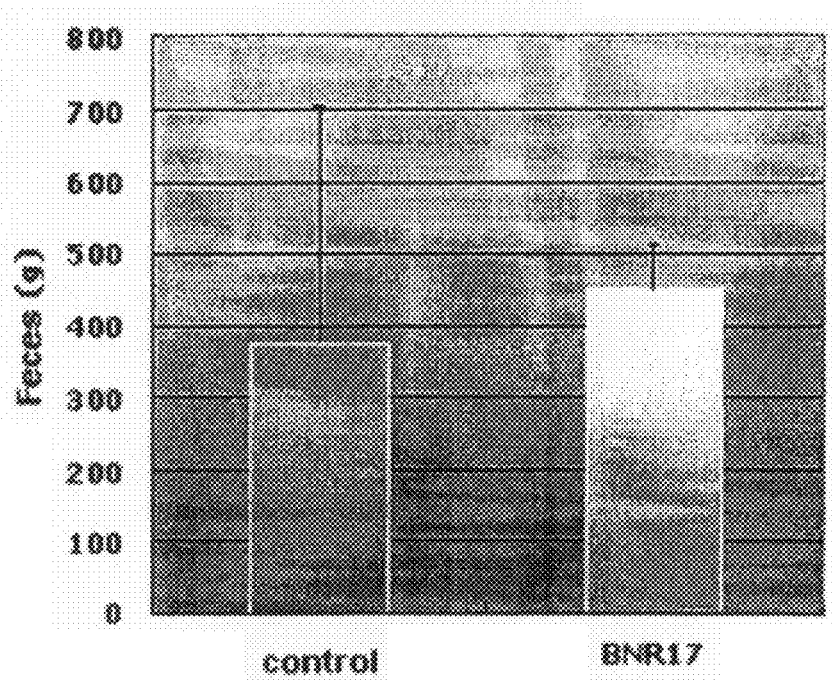
[Fig. 5]

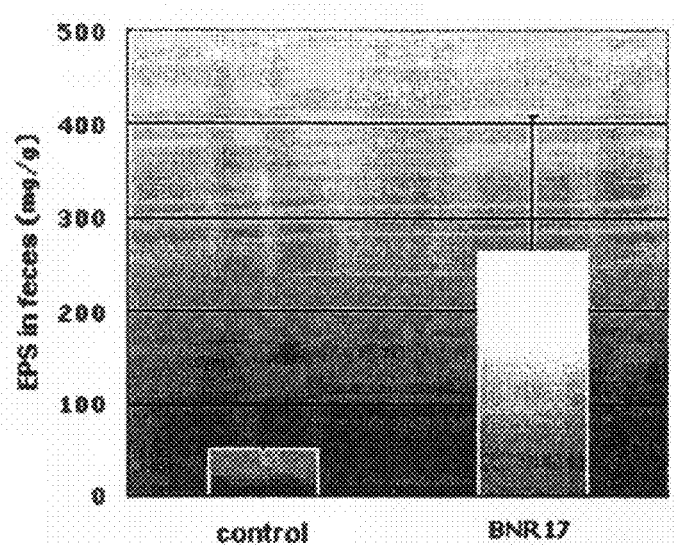
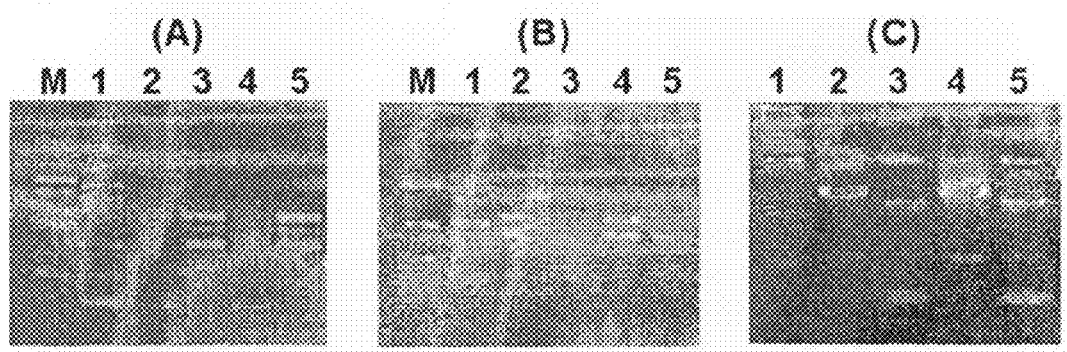

LACTIC ACID BACTERIA ISOLATED FROM MOTHER'S MILK WITH PROBIOTIC ACTIVITY AND INHIBITORY ACTIVITY AGAINST BODY WEIGHT AUGMENTATION

CROSS REFERENCE TO RELATED APPLICATIONS

This application is a 35 U.S.C. §371 National Phase Entry Application from PCT/KR2007/002363, filed May 14, 2007, and designating the United States, which claims priority under 35 U.S.C. §119 to Korean Patent Application No. 10-2006-0073722 filed Aug. 4, 2006, which is incorporated herein in its entirety.

FIELD OF THE INVENTION

The present invention relates to a probiotic lactic acid bacterium, more specifically a novel lactic acid bacterium belonging to *Lactobacillus* sp. isolated from human mother's milk and having excellent probiotic activity such as acid resistance, bile acid resistance and antimicrobial activity and inhibitory activity against body weight augmentation.

DESCRIPTION OF THE RELATED ART

A lactic acid bacterium shares a long history with human, which is the microorganism that is very profitable for human health and thus in the increasing demand. According to the recent progress of the lactic acid bacterium studies, its applicability has been broadened from general foods to health food and medicines. A lactic acid bacterium is exemplified by *Streptococcus* sp., *Pediococcus* sp., *Leuconostoc* sp., *Lactobacillus* sp., *Sporolactobacillus* sp. and *Bifidobacterium* sp. microorganisms.

Lactic acid bacteria inhabit in the animal's intestines where they decompose nutrients and cellulose that the host animal has taken and then use them as an energy source to produce lactic acid and antibiotics in order to inhibit the growth of pathogenic bacteria in the intestine to keep the intestine healthy. The lactic acid bacteria have also been used for stimulation of animal growth, improvement of feed utilization, enhancement of resistance against disease, inhibition of the growth of pathogenic bacteria, reduction of mortality, inhibition of the generation of toxic substances and production of various vitamins.

However, to be effective in the intestine, the incoming lactic acid bacteria from outside have to arrive to the intestines safe and be attached onto the mucous membrane to be functioning. To do so, lactic acid bacteria have to be the one that is able to adhere directly onto the mucous membrane of the intestine, has to be less destroyed by gastric acid when it is orally administered, has to have strong resistance against bile acid and has to have strong antimicrobial activity against pathogens.

When lactic acid bacteria are used for food or medicine for human health, they are supposed to be isolated from human for better effect. In particular, the lactic acid bacteria isolated from mother's milk have been acknowledged to be more effective and safer. However, the human originated lactic acid bacteria have been mostly isolated from adult's feces or breast-feeded infant's feces. The lactic acid bacteria isolated from mother's milk are mostly *Lactobacillus reuteri* and other lactic acid bacteria have hardly been reported.

Meanwhile, obesity is a chronic disease whose cause has not been exactly disclosed but whose development is believed to be attributed to the co-work of several different factors. Obesity might cause hypertension, diabetes, cardiovascular disease, galstone, osteoarthritis, sleep spnea syndrome, breathing disorder, prostatic cancer, breast cancer, colon cancer, etc. The conventional methods hired for the prevention and treatment of obesity are largely diet-exercise therapy, surgical operation, drug therapy, etc. The diet-exercise therapy is to encourage taking low-calorie-low fat food and physical exercise to consume oxygen. This method requires patience since it has to be carried out repeatedly and persistently and that is why this method seems to be ineffective for the general public. The surgical operation is to eliminate body fat by surgery. This method has an advantage of obtaining the desired results in a short time but at the same time has disadvantages of painful surgery, doubt of the continuance of the effect and high costs. The drug therapy needs careful attention because it carries many side effects.

Recently, studies on polysaccharides produced by lactic acid bacteria have been actively undergoing. The mechanism that lactic acid bacteria produce extracellular polysaccharides is known to be very complicated. There are huge differences in productivity and the structure of the polysaccharides according to the kinds of lactic acid bacteria. Polysaccharides produced by lactic acid bacteria have been reported to have anticancer activity and immune enhancing activity (Kitazawa, H. Int. J. Food Microbiol., 1998. 40. 169-175, Hosono, A. Biosci. Biotechnol. Biochem., 1997. 61. 312-316, Chabot, S. Lait. 2001. 81. 683-697). It is also expected to be very safe to take the polysaccharides produced by lactic acid bacteria because lactic acid bacteria themselves are classified as GRAS (Generally Recognized As Safe).

SUMMARY OF THE INVENTION

The present invention relates to a lactic acid bacterium isolated from human mother's milk, and it is an object of the present invention to provide a lactic acid bacterium that has strong resistance against acid, pH and bile acid and strong adherence to intestines so as to convert low-molecular carbohydrates decomposed by a digestive enzyme into high-molecular polysaccharides and to excrete the polysaccharides instead of letting it be absorbed in the body.

DETAILED DESCRIPTION OF THE PREFERRED EMBODIMENTS

To achieve the above object, the present invention provides a *Lactobacillus gasseri* BNR17 strain, the lactic acid bacterium isolated from human mother's milk.

The lactic acid bacteria strain of the present invention has following characteristics.

① Morphology—morphology after culture at 37° C. for 24 hours on the *Lactobacilli* MRS agar plate medium:
  i. Shape, size and color of colony: round, 0.5 mm×2 mm, milk-white color, smooth surface.
  ii. Gram staining: positive.
  iii. Type: rod type (*Bacillus*).
  iv. Sporulation: no.
  v. Mobility: no.

② Physiological properties
  i. Growth temperature: 25~45° C.
  ii. Growth pH: pH 4.0~10.0
  iii. Optimum growth temperature: 37~40° C.
  iv. Optimum growth pH: pH 6.0~8.0

③ Influence of oxygen: facultative anaerobic.

④ Sugar availability:
  Glycerol −, Ribose −, Adonitol −, Galactose +, D-Glucose +, D-Fructose +, D-Mannose +, Mannitol −, Sorbitol −, N-Acetylglucoside +, Esculin +, Salicin +, Cellobiose +, Maltose +, Lactose +, Melibiose −, Saccharose +, Trehalose +, Inulin −, Melezitose −, Raffinose −, Starch −, β-Gentiobiose −, D-Turanose +, D-Tagatose +

⑤ Acid resistance: survived at pH 2.0.

⑥ Bile acid resistance: survived at 0.3% of bile acid.

⑦ Adherence to intestines: adhered to Caco-2 cells, the human intestinal epithelial cells.

⑧ Antibiotic resistance: resistant to Gentamycin, Kanamycin, Streptomycin, Bacitracin, Neomycin, Nalidixic acid, Ciprofloxacin, Polymixcin B and Trimethoprim.

sensitive to Erythromycin, Penicillin, Tetracycline, Ampicillin, Chloramphenicol, Vancomycin and Cefoxitin, Rifampin.

⑨ Antimicrobial activity to pathogenic bacteria: antimicrobial activity to *E. coli, S. aureus, S. typhimurium, B. cereus, L. monocytogenes*, and *P. mirabilis*.

⑩ Presence of antimicrobial peptide: The gene corresponding to gassericin T of bacteriocin, one of antimicrobial peptide components of lactic acid bacteria, is detected by PCR.

⑪ Polysaccharide generation: The lactic acid bacterium of the present invention produces approximately 520 mg/L of polysaccharides after 24 hours of culture on the MRS medium supplemented with 2% glucose. The polysaccharides were composed mainly of glucose, mannose, galactose, fucose, arabinose and D-glucosamine. The polysaccharides produced by the lactic acid bacterium of the present invention are not decomposed by digestive enzymes such as α-amylase and pancreatine.

Koreans have different diet habit with westerners. So, it is clear and natural that the lactic acid bacterium isolated from Koreans have different dietary habits with westerners. So, it is clear and natural that the lactic acid bacterium isolated from Korean best fits to Korean. The lactic acid bacterium isolated from Korean mother's milk fulfills every required fundamental condition for probiotic lactic acid bacterium, resulting in the best health enhancing effect for Korean. The present inventors named such lactic acid bacterium having the above characteristics as "*Lactobacillus gasseri* BNR17" and deposited at Korean Collection for Type Cultures (KCTC) of Korea Research Institute of Biotechnology and Bioscience (KRIBB), located at #52, Oun-dong, Yusong-ku, Taejon 305-333, Republic of Korea, on Jan. 23, 2006 (Accession No: KCTC 10902BP).

The present invention also provides a composition containing an effective dose of the lactic acid bacterium. The composition of the present invention can be provided in the forms of food, food additives, animal feeds and animal feed additives.

The novel lactic acid bacterium provided by the invention, *Lactobacillus gasseri* BNR17 (Accession No: KCTC 10902BP) has excellent acid resistance, bile acid resistance and antimicrobial activity, making it an excellent candidate as a seed for the production of various fermented milk products and other fermented foods. The fermented milk products herein can be exemplified by yoghurt, calpis, cheese and butter, and the other fermented foods herein can be exemplified by tofu, soy bean paste, Chungkukjang, jelly and Kimchi, but not always limited thereto. The fermented milk products and fermented foods can be easily produced by the conventional method only with substituting the strain with the lactic acid bacterium of the invention.

According to a preferred embodiment of the present invention, approximately 7.7% weight gaining inhibitory effect was observed in the experimental group rats administered with *Lactobacillus gasseri* BNR17, compared with the control group rats administered with PBS (phosphate-buffered saline)(see Table 6). In addition to the weight gaining inhibitory effect, diet efficiency in the experimental group was also reduced significantly, compared with the control group. Polysaccharides included in feces of both experimental and control groups were examined. As a result, the polysaccharide content in feces of experimental group was higher than that of control group (see FIG. 6). These results indicate that the indigestible polysaccharide producing capacity of *Lactobacillus gasseri* BNR17 plays a certain role in weight regulation. In the meantime, no superficial side effects have been detected in the experimental group rats taking *Lactobacillus gasseri* BNR17 and the weight of each organ was not much different from that of control group (see Table 7 and Table 8). Microorganism transition, one of major concerns when human takes a microorganism, was not observed, suggesting that the lactic acid bacterium of the present invention is very safe for human to take (see FIG. 7).

The lactic acid bacterium food products of the present invention can be produced as an edible form of composition either containing *Lactobacillus gasseri* BNR17 alone or with any acceptable carrier. The lactic acid bacterium of the invention can be added to the food that does not contain any probiotic bacteria or the food that already contains several kinds of probiotic bacteria. The microorganism that can be co-used with the lactic acid bacterium of the invention to produce the lactic acid bacterium food has to be appropriate for intake by human or animals and have probiotic activity such as inhibiting pathogenic bacteria or improving the balance of microorganisms in the mammal's intestines, but not always limited thereto. The probiotic microorganism is exemplified by yeasts such as *Saccharomyces, Candida, Pichia* and *Torulopsis*; fungi such as *Aspergillus, Rhizopus, Mucor* and *Penicillium*; and bacteria belonging to *Lactobacillus, Bifidobacterium, Leuconostoc, Lactococcus, Bacillus, Streptococcus, Propionibacterium, Enterococcus* and *Pediococcus*. Preferably, the probiotic microorganism can be selected from the group consisting of *Saccharomyces cerevisiae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei, Lactobacillus curvatus, Lactobacillus delbruckii, Lactobacillus johnsonii, Lactobacillus farciminus, Lactobacillus gasseri, Lactobacillus helveticus, Lactobacillus rhamnosus, Lactobacillus reuteri, Lactobacillus sakei, Lactococcus lactis* and *Pediococcus acidilactici*. It is more preferred to add a probiotic microorganism mixture having excellent probiotic activity and immune enhancing activity as well as anticancer activity to the lactic acid bacterium food of the invention, resulting in greater effect. A carrier acceptable for the lactic acid bacterium food of the invention is exemplified by a diluent, a high-fiber additive, an encapsulant and a lipid, which have been well informed to those skilled in the art. The lactic acid bacterium of the invention, *Lactobacillus gasseri* BNR17, can be formulated as capsules, culture suspension or dried powder.

In addition, the composition containing the lactic acid bacterium of the invention can be prepared as animal feeds or animal feed additives.

The animal feed additive of the invention can be prepared in dried or liquid form and can contain other non-pathogenic microorganisms in addition to the *Lactobacillus gasseri* BNR17. The addable microorganism can be selected from the group consisting of *Bacillus subtilis* producing protease, lipase and sugar converting enzyme; *lactobacillus* strain having organic decomposition activity and maintaining physical activities under anaerobic condition; filamentous fungi such as *Aspergillus oryzae* (Slyter, L. L. J. Animal Sci. 1976, 43. 910-926) contributing to the increase of milk and weight of cattle and feed digestibility as well; and yeast such as *Saccharomyces cerevisiae* (Johnson, D. E et al. J. Anim. Sci., 1983, 56, 735-739; Williams, P. E. V. et al, 1990, 211).

The animal feed additive of the present invention can additionally include one or more enzyme products in addition to the *Lactobacillus gasseri* BNR17. The addable enzyme product can be in dried or liquid form, which is selected from the group consisting of lipase, phytase decomposing phytic acid into phosphate and inositol phosphate, amylase hydrolyzing $\alpha$-1,4-glycoside bond included in starch and glycogen, phosphatase hydrolyzing organic phosphoric acid ester, carboxymethylcellulase decomposing cellulose, xylase decomposing xylose, maltase hydrolyzing maltose into two glucoses and invertase hydrolyzing saccharose into glucose-fructose.

When the lactic acid bacterium of the invention is added to the animal feed as an additive, the proper feed raw material is selected from the group consisting of crops, soybean protein, peanut, green pea, sugar beet, pulp, crop byproduct, animal intestine powder and fish powder. At this time, these materials can be used as they are or after being processed. To process the animal feed, for example, raw material for feed is compressed by pressure to be discharged, but not always limited thereto. In the case of using a protein as a raw material, extrusion is preferred. Particularly, extrusion is to denaturate a protein by heat-treatment, resulting in the destruction of anti-enzyme factors. More specifically, in the case of using a soybean protein, extrusion improves the digestibility of the protein, inactivates anti-nutrition factors such as trypsin inhibitor, one of protease inhibitors, and increases digestibility by a protease, resulting in the increase of nutritional value of the protein.

The present invention further provides a pharmaceutical composition for the prevention and treatment of obesity which contains the effective dose of *Lactobacillus gasseri* BNR17 (Accession No: KCTC 10902BP).

The *Lactobacillus gasseri* BNR17 of the invention is generally administered as a tablet or a capsule prepared by mixing the lactic acid bacterium with a pharmaceutically acceptable carrier, an excipient or another effective supplementary component.

The acceptable carrier, excipient or diluent for the pharmaceutical composition of the invention is exemplified by lactose, dextrose, sucrose, sorbitol, mannitol, starch, acacia gum, calcium phosphate, alginate, tragacanth gum, gelatin, calcium silicate, microcrystalline cellulose, polyvinylpyrrolidone, cellulose, water, syrup, methylcellulose, methylhydroxybenzoate, propylhydroxybenzoate, talc, magnesium stearate or mineral oil. The microorganism composition of the invention can additionally include lubricants, wetting agents, emulsifying agents, suspension agents, preserving agents, sweetening agents or flavors. The composition of the invention can be prepared in the form of enteric coated preparation in order for the composition to pass through the stomach and reach the small intestine safely and to release microorganism, the active ingredient, therein fast and easy, according to the conventional method well known to those skilled in the art.

The microorganism composition of the present invention can also be prepared in the form of a capsule, according to the conventional capsule production method. For example, a standard carrier is used for the preparation of a pellet containing the freezing-dried microorganism of the invention, which fills soft gelatin capsules. Another example is that the microorganism of the invention is mixed with a pharmaceutically acceptable carrier, for example soluble gum, cellulose, silicate or oil, to prepare suspension or dispersing solution, which fills soft gelatin capsules.

The pharmaceutical composition of the present invention can be provided as a unit drug form for oral administration as an enteric coated preparation. "Enteric coating" herein indicates that a drug is not decomposed by gastric acid and maintained as being coated but is decomposed in the small intestine to release active ingredients therein, which includes every kind of pharmaceutically acceptable coatings. "Enteric coating" of the invention is maintained at least two hours in the artificial gastric juice such as HCl solution (pH 1) at 36-38° C. but the coating is preferably decomposed within 30 minutes in the artificial intestinal juice such as $KH_2PO_4$ buffer solution (pH 6.8).

Enteric coating of the invention is performed, in which one core is coated by 16-30 mg, preferably 16-20 mg or less than mg of the composition. The preferable thickness of the coating is 5-100 µm and more preferably 20-80 µm for the best results. Materials for the enteric coating can be selected among the well-informed high molecular substances. Those high molecular substances are described in numbers of references (L. Lachman, et al., The Theory and Practice of Industrial Pharmacy, $3^{rd}$ edition, 1986, pp. 365~373; H. Sucker, et al., Pharmazeutische Technologie, Thieme, 1991, pp. 355-359; Hagers Handbuch der pharmazeutischen Praxis, $4^{th}$ edition, Vol. 7, pp. 739-742, and 766-778, (SpringerVerlag, 1971); and Remington's Pharmaceutical Sciences, $13^{th}$ edition, pp. 1689~1691 (Mack Publ., Co., 1970)), which can be exemplified by cellulose ester derivatives, cellulose ether, methylacrylate copolymer of acrylic resin and copolymer of maleic acid and phthalic acid derivatives.

The enteric coating of the invention can be performed by the conventional method which is spraying the coating solution onto a core. The acceptable solvent for the enteric coating is selected from the group consisting of alcohol such as ethanol, ketone such as acetone, halogenized hydrocarbon such as $CH_2Cl_2$ and a mixture thereof. A softener such as di-n-butylphthalate or triacetine can be added to the coating solution at the ratio of 1:0.05-0.3 (coating material:softener). It is preferred to spray serially and the amount of spry is determined by considering the coating conditions. Spraying pressure can be regulated and generally 1-1.5 bar is considered to give best results.

The "pharmaceutically effective dosage" of the invention indicates the minimum amount of the microorganism of the invention that is able to reduce low-sugar carbohydrates to be absorbed into the intestines of mammals. The dosage of the microorganism, which is delivered to the human body by the composition of the invention, can be regulated according to the administration pathway and subjects.

The composition of the invention can be administered to a subject at least once a day, everyday. Unit dosage indicates the unit separated physically to be appropriate for unit administration to a subject, either human or other mammals, and each unit contains a required amount of acceptable carrier and a required amount of the microorganism of the invention for the treatment effect. The unit dosage for oral administration of the composition of the invention is preferably 0.1-10 g and more preferably 0.5-5 g. The pharmaceutically effective dosage of the microorganism of the invention is 0.1-10 g/day. However, the dosage might vary according to the weight of a patient, the severity of obesity, and effective supplementary ingredients and microorganisms. The one day dosage can be divided into several sub-units so that they can be administered serially if necessary. Thus, the dosage of the composition of the invention cannot limit the spirit and scope of the invention in any way.

The regular administration of the composition of the invention results in the interruption of the absorption of saccharides inside the human body by releasing microorganisms to compete and form microflora, which interrupts the absorption, and further involves in the convert of monosaccharides such as carbohydrate into polysaccharides so as to inhibit the absorption thereof. In addition, dietary fiber produced by the microorganism provides preferable conditions for useful enterobacteria to grow with stimulating intestinal motility. Therefore, the composition of the invention can be effectively used for the prevention and treatment of obesity.

To maximize the weight reducing effect or obesity preventive effect of the pharmaceutical composition, any weight reducing agent known to those skilled in the art can be additionally included in the composition by a proper amount. The amount can be determined by those skilled in the art after multiple tests. The effective ingredient as an additive, the weight reducing agent, is preferably selected from the group consisting of conjugated linoleic acid, polydextrose, inulin, guar gum, arabic gum, L-carteine, grape seed extract, fructooligosaccharide, xylooligosaccharide, raffinose, gluconic acid, champignon, polyanthocyanidine, lactulose, lactitol, lactosucrose, *Angelica gigas* extract, *Hovenia dulcis* extract and tangerine peel extract, but not always limited thereto.

The present invention also provides a culture solution prepared by culturing *Lactobacillus gasseri* BNR17 (Accession No: KCTC 10902BP). The medium used to prepare the culture solution is not limited, and any medium that contains a medium for microorganism culture can be used. The culture solution of the invention can additionally contain any additive if necessary for a specific use. For example, to maximize the weight reducing effect, any weight reducing agent well known to those skilled in the art can be added to the culture solution and at this time the content of the agent can be determined by those skilled in the art after examining the effective dose range through repeated tests.

The present invention also provides a bacteriocin peptide produced by the lactic acid bacterium of the invention and a gene encoding the same. The present inventors named the bacteriocin peptide as "gassericin BNR17" which was confirmed to have the nucleotide sequence represented by SEQ. ID. NO: 5. The nucleotide sequence of the gassericin BNR17 was compared with that of the conventional antimicrobial peptide, gassericin T (NCBI Blast Search No. AB029612, SEQ. ID. NO: 6), and as a result, the gassericin BNR17 had approximately 98% homology with the gassericin T.

The present invention further provides a recombinant vector containing the gassericin BNR17 gene.

The recombinant vector of the present invention can be prepared by inserting the gene having the nucleotide sequence represented by SEQ. ID. NO: 5 into a general expression vector for *E. coli*. The mother vector for the construction of the recombinant vector is not limited to a specific one, and almost every microorganism expression vector can be used but an *E. coli* expression vector is preferred.

The present invention also provides a transformant transformed with the recombinant vector.

The transformant of the invention can be easily generated by introducing the above recombinant vector into a random host cell. The host cell herein can be selected from the group consisting of eukaryotic or prokaryotic cells and multicellular animal originated cell lines, but not always limited thereto.

BRIEF DESCRIPTION OF THE DRAWINGS

The application of the preferred embodiments of the present invention is best understood with reference to the accompanying drawings, wherein:

FIG. 1 is a diagram showing the sequence comparison between *Lactobacillus gasseri* BNR17 of the invention (upper sequence in figure, SEQ. ID. NO: 1) and *Lactobacillus gasseri* KC26 (NCBI GENBANK Accession No: AF243156, lower sequence in figure, SEQ. ID. NO: 2) 16s rRNAs.

FIG. 2 is a microphotograph showing the enteric adherence of *Lactobacillus gasseri* BNR17 of the invention.

FIG. 3 is a set of photographs showing that *Lactobacillus gasseri* BNR17 of the invention has antimicrobial activity against various pathogenic bacteria.

FIG. 4 is a graph showing the glucose consumption and polysaccharide production according to the growth of *Lactobacillus gasseri* BNR17 of the invention.

■; cell growth, ♦; glucose concentration, ▲; EPS (polysaccharide) concentration

FIG. 5 is a graph showing the amount of feces of a rat taking *Lactobacillus gasseri* BNR17 of the invention.

FIG. 6 is a graph showing the EPS (polysaccharide) concentration in the feces of a rat taking *Lactobacillus gasseri* BNR17 of the invention.

FIG. 7 is a set of electrophoresis photographs showing the RAPD-PCR profiles of colonies isolated from other organs than the small intestine of a rat taking *Lactobacillus gasseri* BNR17 of the invention, in which primers represented by SEQ. ID. NO: 7 (A), NO: 8 (B) and NO: 9 (C) were used.

Lane 1; *Lb. gasseri* BNR17, Lanes 2-5; colonies isolated from other organs than the small intestine of a rat taking *Lb. gasseri* BNR17, M; DNA size marker.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Lactic Acid Bacterium Isolation from Human Mother's Milk

Human mother's milk was taken from a woman delivered of a baby not more than two weeks ago. Then, the mother's milk was diluted with PBS and the undiluted milk and diluted milk were distributed on a *lactobacillus* selection medium respectively. The medium was cultured at 37° C. for 2-3 days and the colonies generated therein were sorted by morphology and color. The isolated colonies were Gram-stained and observed under a microscope to select those colonies that were Gram-positive and had rod-shaped structure. The selected colonies were cultured in MRS liquid medium (pH 6.8) at 37° C. for 24 hours. Colonies in the culture solution under the pH lower than 4.5 were selected. The colonies were cultured in MRS medium (pH 2.0) for 2 hours, followed by further culture in MRS medium supplemented with 0.3% oxgall for 9 hours. The survived *lactobacillus* strain that exhibited acid resistance and bile acid resistance was isolated and identified by 16S rRNA sequencing. As a result, the strain was confirmed to belong *Lactobacillus gasseri* species (SEQ. ID. NO: 1, FIG. 1) and named as "*Lactobacillus gasseri* BNR17".

Example 2

Sugar Utilization of the Isolated Lactic Acid Bacterium

Sugar utilization of *Lactobacillus gasseri* BNR17 of the invention isolated above was investigated by comparing with other standard strains using API50CHL kit (Biomerieux, France) and the results are shown in Table 1. In Table 1, 5314 indicates *Lactobacillus gasseri* CECT5714; 5315 indicates *Lactobacillus gasseri* CECT5715; 11413 indicates *Lactobacillus gasseri* LMG11413; 18194 indicates *Lactobacillus gasseri* LMG18194; 4479 indicates *Lactobacillus gasseri* CECT4479; 18176 indicates *Lactobacillus gasseri* LMG 18176; and 13047 indicates *Lactobacillus gasseri* LMG13047.

TABLE 1

|  | BNR17 | 5714 | 5715 | 11413 | 18194 | 4479 | 18176 | 13047 |
|---|---|---|---|---|---|---|---|---|
| Glycerol | 0 | 0 | 0 | 0 | 0 | 0 | 0 | 0 |
| Erythritol | 0 | 0 | 0 | 0 | 0 | 0 | 0 | 0 |
| *D-Arabinose* | 0 | 0 | 4 | 0 | 0 | 0 | 0 | 0 |
| *L-Arabinose* | 0 | 0 | 4 | 0 | 0 | 0 | 0 | 0 |
| Ribose | 0 | 0 | 0 | 0 | 0 | 0 | 0 | 0 |
| D-Xylose | 0 | 0 | 0 | 0 | 0 | 0 | 0 | 0 |
| L-Xylose | 0 | 0 | 0 | 0 | 0 | 0 | 0 | 0 |
| Adonitol | 0 | 0 | 0 | 0 | 0 | 0 | 0 | 0 |
| β-Methyl-xyloside | 0 | 0 | 0 | 0 | 0 | 0 | 0 | 0 |
| Galactose | 5 | 5 | 5 | 5 | 5 | 5 | 5 | 5 |
| D-Glucose | 5 | 5 | 5 | 5 | 5 | 5 | 5 | 5 |
| D-Fructose | 5 | 5 | 5 | 5 | 5 | 5 | 5 | 5 |
| D-mannose | 5 | 5 | 5 | 5 | 5 | 5 | 5 | 5 |
| *L-Sorbose* | 0 | 0 | 0 | 5 | 0 | 0 | 0 | 0 |
| Rhamnose | 0 | 0 | 0 | 0 | 0 | 0 | 0 | 0 |
| *Dulcitol* | 0 | 0 | 0 | 4 | 0 | 0 | 0 | 0 |
| Inositol | 0 | 0 | 0 | 0 | 0 | 0 | 0 | 0 |
| *Mannitol* | 0 | 0 | 3 | 5 | 0 | 0 | 0 | 0 |
| Sorbitol | 0 | 0 | 0 | 0 | 0 | 0 | 0 | 0 |
| α-Methyl-D-mannoside | 0 | 0 | 0 | 0 | 0 | 0 | 0 | 0 |
| α-Methyl-D-glucoside | 0 | 0 | 0 | 0 | 0 | 0 | 0 | 0 |
| N-Acetlyglu-cosamine | 5 | 4 | 5 | 5 | 5 | 5 | 5 | 5 |
| *Amygdalin* | 5 | 5 | 5 | 0 | 0 | 5 | 5 | 0 |
| *Arbutine* | 5 | 5 | 5 | 1 | 1 | 5 | 5 | 4 |
| Esculine | 5 | 5 | 5 | 5 | 5 | 5 | 5 | 5 |
| Salicine | 5 | 5 | 5 | 5 | 5 | 5 | 5 | 3 |
| Cellobiose | 5 | 5 | 5 | 5 | 5 | 5 | 5 | 5 |
| Maltose | 5 | 5 | 5 | 5 | 5 | 5 | 5 | 5 |
| *Lactose* | 5 | 0 | 4 | 5 | 5 | 5 | 5 | 0 |
| *Melibiose* | 0 | 0 | 0 | 0 | 0 | 0 | 5 | 0 |
| Saccharose | 5 | 5 | 5 | 5 | 5 | 5 | 5 | 5 |
| Trehalose | 5 | 5 | 5 | 5 | 5 | 5 | 5 | 5 |
| Inuline | 0 | 0 | 0 | 0 | 0 | 0 | 0 | 0 |
| Melezilose | 0 | 0 | 0 | 0 | 0 | 0 | 0 | 0 |
| D-Raffinose | 0 | 0 | 0 | 0 | 0 | 0 | 5 | 0 |
| *Armidon* | 5 | 3 | 5 | 1 | 1 | 5 | 3 | 3 |
| *Glycogene* | 0 | 0 | 0 | 4 | 4 | 0 | 0 | 0 |
| Xylitol | 0 | 0 | 0 | 0 | 0 | 0 | 0 | 0 |
| b-Gentobiose | 5 | 5 | 5 | 5 | 5 | 5 | 5 | 5 |
| *D-Turanose* | 5 | 0 | 0 | 0 | 0 | 0 | 0 | 0 |
| D-Lycose | 0 | 0 | 0 | 0 | 0 | 0 | 0 | 0 |
| *D-Tagatose* | 5 | 5 | 5 | 3 | 3 | 5 | 5 | 5 |
| D-Fucose | 0 | 0 | 0 | 0 | 0 | 0 | 0 | 0 |
| L-Fucose | 0 | 0 | 0 | 0 | 0 | 0 | 0 | 0 |
| D-Arabinol | 0 | 0 | 0 | 0 | 0 | 0 | 0 | 0 |

As shown in Table 1, compared with other *lactobacillus* strains, the *Lactobacillus gasseri* BNR17 of the invention was distinguishable in sugar utilization from others (shown in thick Italics).

Example 3

Enzyme Activity of the Isolated Lactic Acid Bacterium

The enzyme activity of the *Lactobacillus gasseri* BNR17 isolated in Example 1 was compared with those of other standard strains using APIZYM kit (Biomerieux, France) and the results are shown in Table 2. In Table 2, 13134 indicates *Lactobacillus gasseri* LMG13134.

TABLE 2

| | BNR17 | 11413 | 13047 | 13134 | 18176 | 18194 | 4479 | 5714 | 5715 |
|---|---|---|---|---|---|---|---|---|---|
| Control | − | − | − | − | − | − | − | − | − |
| Alkaline phosphates | − | − | − | − | − | − | − | − | − |
| Esterase (C4) | 1 | 2 | 1 | 1 | 1 | 1 | 1 | 1 | 1 |
| Esterase lipase (C8) | − | − | − | 1 | − | − | − | − | − |
| Lipase (C4) | − | − | − | − | − | − | − | − | − |
| Leucine arylamidase | + | + | + | + | + | + | + | + | + |
| *Valine arylamidase* | 1 | 1 | 1 | 3 | 2 | − | − | − | 1 |
| *Cystine arylamidase* | 1 | 1 | 1 | 4 | 2 | 3 | 4 | 1 | 1 |
| Trypsin | − | − | − | − | − | − | − | − | − |
| α-chymotrypsin | − | − | 1 | − | − | − | − | − | − |
| *Acid phosphatase* | + | 1 | 2 | + | − | 1 | 2 | 1 | 1 |
| *Naphthol-As-BI-phosphohydrolase* | + | 1 | + | + | + | − | + | + | + |
| α-galactosidase | + | + | − | − | + | − | + | + | + |
| β-galactosidase | + | 4 | 1 | 3 | − | − | − | − | − |
| β-glucuronidase | − | + | + | − | − | − | − | − | − |
| α-glucosidase | 1 | 1 | + | − | 1 | 2 | 1 | − | 1 |
| β-glucosidase | 3 | + | − | 3 | + | − | 3 | 4 | + |
| *N-acetyl-β-glucosaminidase* | 1 | + | 1 | − | + | − | − | − | 1 |
| α-mannosidase | − | − | − | − | − | − | − | − | − |
| α-fucosidase | − | − | − | − | − | − | − | − | − |

As shown in Table 2, the *Lactobacillus gasseri* BNR17 of the invention was distinguishable in enzyme activity from other strains (shown in thick Italics).

Example 4

Acid Resistance and Bile Acid Resistance

To investigate acid resistance and bile acid resistance of the strain of the invention, *Lactobacillus gasseri* BNR17 was inoculated in 4 ml of MRS liquid medium and cultured at 37° C. for 18-20 hours. Some of the culture solution was re-inoculated in another MRS medium with regulated pH of 2.0 at the concentration of $10^7$ CFU/ml and cultured at 37° C. for 2 hours. The number of live cells was counted using MRS agar plate. The culture solution tested for acid resistance was used again for centrifugation. The cells were recovered and inoculated in MRS liquid medium (pH 6.8) supplemented with 0.3% oxgall, followed by culture at 37° C. for 9 hours. The number of live cells was also counted using MRS agar plate. The results are shown in Table 3.

TABLE 3

| | Before treatment | Treatment at pH 2.0 | 0.3% oxgall treatment |
|---|---|---|---|
| BNR17 | $3.1 \times 10^7$ | $2.1 \times 10^7$ | $1.5 \times 10^7$ |

As a result, even after the treatment with strong acid (pH 2.0), the *Lactobacillus gasseri* BNR17 exhibited high survival rate, and so did in the medium supplemented with 0.3% oxgall.

Example 5

Enteric Adherence

The strain of the invention was inoculated on the plate on which a human intestinal epithelial cell line CaCo-2 was cultured in PRMI1640 (Gibco) at the concentration of $10^7$ CFU/ml. The strain was cultured at 37° C. for one hour, followed by washing three times with PBS to eliminate non-adhered cells. The sample was fixed with methanol and then stained with crystal violet, followed by observation under a microscope. As a result, the *Lactobacillus gasseri* BNR17 of the invention was confirmed to be very well adhered on CaCo-2 cells (FIG. 2).

Example 6

Antimicrobial Activity Against Pathogenic Bacteria

*E. coli, S. aureus, S. typhimurium, B. cereus, L. monocytogenes* and *P. mirabilis* were cultured at 37° C. for 18 hours in BHI liquid medium (Difco) and then inoculated in 6 of 5 ml BHI agar media (agar content: 0.7%) respectively at the concentration of $10^5$ CFU/ml. These media were overlapped on 6 plates with BHI agar media (agar content: 1.5%) fixed thereon. After hardening those 6 plate media, a well of 4 mm in diameter was made in each medium, in which 40 µl of the supernatant (2×) of lactic acid bacterium culture solution cultured at 37° C. for 24 was added, followed by culture at 37° C. for 5 hours.

As a result, a clear growth inhibition ring was observed around the well, suggesting that the strain of the invention has antimicrobial activity against various pathogenic bacteria (Table 4 and FIG. 3).

TABLE 4

| Pathogenic bacteria | Diameter of growth inhibition ring (mm) |
|---|---|
| *E. coli* KCTC1039 | 16 |
| *B. cereus* KCTC1526 | 16 |
| *L. monocytogenes* KCTC3710 | 12 |
| *P. mirabilis* KCTC2510 | 14 |
| *S. aureus* KCTC1928 | 6 |
| *S. typhimurium* KCTC2421 | 18 |

Example 7

Antibiotic Resistance

Lactobacillus gasseri BNR17 culture solution was smeared on MRS agar plate by using a swab, on which a disc containing erythromycin, penicillin, gentamycin, kanamycin, streptomycin, bacitracin, chloramphenicol, vancomycin, tetracycline, ampicillin, cefoxitin, rifampin, neomycin, nalidixic acid, ciprofloxacin, polymixcin B or trimethoprim was placed, followed by culture at 37° C. for 24 hours.

As a result, Lactobacillus gasseri BNR17 of the invention was confirmed to have resistance against gentamycin, streptomycin and trimethoprim.

Example 8

Detection of the Antimicrobial Peptide Gene

Bacteriocin gene was investigated by PCR performed by using the Lactobacillus gasseri BNR17 genomic DNA as a template and primers represented by SEQ. ID. NO: 3 and NO: 4 which were specific to the nucleotide sequence of a gene of bacteriocin known as an antimicrobial peptide produced by Lactobacillus gasseri species.

As a result, the PCR product corresponding to gassericin was confirmed and represented by SEQ. ID. NO: 5. The nucleotide sequence was compared with that of gassericin T (NCBI Blast Search No. AB029612) represented by SEQ. ID. NO: 6 and confirmed to have approximately 98% homology.

Example 9

β-glucuronidase Activity

β-glucuronidase produced by enterobacteria has been known as one of oncogenic enzymes and thus the strain that has this enzyme activity is considered as a harmful strain. To investigate whether the Lactobacillus gasseri BNR17 of the invention has β-glucuronidase activity or not, the enzyme activity of Lactobacillus gasseri BNR17 was tested using API ZYM kit (Biomerieux, France).

As a result, the strain of the invention was confirmed not to have β-glucuronidase activity, suggesting that the strain was safe (Table 5).

TABLE 5

| Enzyme | Activity |
| --- | --- |
| α-galactosidase | Positive |
| β-galactosidase | Positive |
| β-glucuronidase | Negative |
| α-glucosidase | Negative |
| β-glucosidase | Positive |

Example 10

Glucose Consumption and Polysaccharide Production

Lactobacillus gasseri BNR17 was inoculated in MRS medium (Difco) prepared by adding 2% glucose (w/v) at the concentration of $10^6$ cfu/ml and cultured for 96 hours, during which the cell number was measured stepwise and at the same time glucose consumption and extracellular polysaccharide (EPS) production were measured as well.

As a result, the highest level of Lactobacillus gasseri BNR17 was observed on the $12^{th}$ hour of culture and since then the level had been decreased. Glucose concentration was rapidly reduced after 7 hours of culture and no changes of glucose concentration were detected after 36 hours, suggesting that most of glucose was consumed within 36 hours from the culture started. EPS production was maximized on the $24^{th}$ hour (the highest level: 520 mg/k) and was slightly reduced on the $36^{th}$ hour but increased again thereafter. It was presumed to be attributed to autolysis of the cells causing various polysaccharides in the cells to be released into the culture solution (FIG. 4).

Example 11

Decomposition of the Polysaccharide Produced by Lactobacillus Gasseri BNR17 by a Digestive Enzyme 100 mg of each α-amylase (Sigma) and pancreatin (Sigma) was dissolved in 0.05 M phosphate buffer (pH 7.0). 50 μl of the above enzyme solution and 150 μl of 0.05 M phosphate buffer (pH 7.0) were added to 200 μl of polysaccharide (EPS) solution extracted from the supernatant of Lactobacillus gasseri BNR17 culture solution, followed by reaction at 37° C. for one hour. The reaction mixture was heated at 100° C. for 15 minutes to inactivate enzymes therein, followed by cooling at room temperature. Glucose concentration was measured with a glucose kit (Sigma).

As a result, glucose was not detected in the polysaccharide solution before the treatment of each digestive enzyme, while 3.70 mg/l and 19.1 mg/l of glucose were respectively detected after the treatment of pancreatin and α-amylase. This result indicates that the polysaccharide produced by Lactobacillus gasseri BNR17 was hardly decomposed by a digestive enzyme.

Example 12

Weight Gaining Inhibitory Effect of Lactobacillus Gasseri BNR17

8 week old male SD rats were grouped into two. One group was orally administered with PBS only (pH 7.4) and the other group was orally administered with PBS suspended with $10^9$ CFU/ml of Lactobacillus gasseri BNR17, everyday for 8 weeks. Changes of weights, food intakes, and blood chemical values such as cholesterol level were measured once a week. The amounts of feces and EPS in feces were also measured to investigate the relation of weight gaining inhibitory effect of Lactobacillus gasseri BNR17 and polysaccharide production capacity thereof. 8 weeks later, all the test animals were sacrificed and dissected to extract the liver, kidney, spleen, MLN (mesenteric lymph node), which were measured their weights. Some of each organ extracted was homogenized and smeared on LBS agar, a lactobacillus selection medium, which was then cultured and RAPD (random amplified polymorphic DNA)-PCR profiles of the generated colonies were investigated. The result was compared with the RAPD-PCR profile of Lactobacillus gasseri BNR17 to investigate whether the strain was transferred to other organs.

As a result, approximately 179.1% weight increase was observed for 8 weeks in the control group orally administered with PBS only, while approximately 171.6% weight increase was observed in the experimental group orally administered with Lactobacillus gasseri BNR17 (Table 6). The experimental group also exhibited lower rates of one-day weight increase and food efficiency ratio than the control.

TABLE 6

| Group | Weight (g) | | Weight gaining (g/day) | Food efficiency ratio** |
|---|---|---|---|---|
| | Initial weight | Final weight* | | |
| Control | 221.20 ± 3.759 | 393.73 ± 4.860 | 3.081 | 0.131 ± 0.078 |
| BNR17 | 223.66 ± 10.077 | 380.85 ± 21.517 | 2.807 | 0.115 ± 0.067 |

In Table 6, food efficiency ratio (FER) indicates weight gaining (g day)/food intake (g day). *P<0.05, **P<0.05.

The results of measuring the amounts of feces and EPS in feces of both the control and the experimental groups are shown in FIG. 5 and FIG. 6. The amounts of feces were not much different between the control and the experimental groups, but the ESP amount was significantly increased in the experimental group administered with *Lactobacillus gasseri* BNR17. This result indicates that *Lactobacillus gasseri* BNR17 converts sugar components taken inside body into indigestible polysaccharides so as to release the polysaccharides out of the body, resulting in the decrease of in vivo absorption rate and inhibition of weight gaining.

To examine safety of the strain for human administration, blood chemical values and organ weights were measured. Each levels and values were similar in the control and the experimental groups, suggesting that the strain did not cause side effects (Table 7 and Table 8).

TABLE 7

| Group | Cholesterol (mg/dL) | Glucose (mg/dL) | HDL (mg/dL) | LDL (mg/dL) | Total protein (g/dL) | Triglyceride (mg/dL) |
|---|---|---|---|---|---|---|
| Control | 99.7 ± 11.7 | 88.9 ± 12.1 | 38.5 ± 3.5 | 21.5 ± 1.6 | 8.6 ± 0.3 | 115.9 ± 11.0 |
| BNR17 | 96.3 ± 6.3 | 79.2 ± 4.1 | 40.8 ± 1.8 | 20.8 ± 3.1 | 9.0 ± 0.3 | 132.6 ± 5.5 |

TABLE 8

| Group | Liver | Kidney | Spleen |
|---|---|---|---|
| Control | 0.029 ± 0.001 | 0.007 ± 0.000 | 0.002 ± 0.000 |
| BNR17 | 0.027 ± 0.003 | 0.007 ± 0.001 | 0.002 ± 0.000 |

In Table 8, each number indicates organ weight (g)/rat weight (g).

To investigate whether the strain was transferred to other organs, RAPD-PCR profiles of colonies of each organ tissue cultured on LBS agar plate were investigated by using primers p1, p2 and OPL5 respectively represented by SEQ. ID. NO: 7-NO: 9. PCR using the primers p1 and p2 was performed as follows; 94° C. (2 minutes), 36° C. (5 minutes), 72° C. (5 minutes)—4 cycles/94° C. (1 minute), 36° C. (1 minute), 72° C. (2 minutes)—36 cycles. PCR using the primer OPL5 was performed as follows; 94° C. (2 minutes)—1 cycle/94° C. (40 seconds), 45° C. (1 minute), 72° C. (1 minute)—2 cycles/94° C. (40 seconds), 52° C. (1 minute), 72° C. (3 minutes)—30 cycles/70° C. (5 minutes)—1 cycle.

As a result, no colonies exhibited similar profiles to BNR17 (FIG. 7). Thus, BNR17 was confirmed to be safe strain which is not transferred to other organs except the small intestine when it is taken.

Manufacturing Example 1

Preparation of Fermented Milk

Raw milk in which milk solid non fat content was regulated by 8-20% using powdered skim milk was sterilized at 72-75° C. for 15 seconds. The sterilized raw milk was cooled down to the proper temperature, to which *Lactobacillus gasseri* BNR17 of the invention was inoculated at the concentration of $10^6$ cfu/ml, followed by culture until pH reached 4-5. Upon completion of the culture, the culture solution was cooled down. In the meantime, 0.1-50 weight % of fruit juice concentrate, 0.1-20 weight % of dietary fiber, 0.5-30 weight % of glucose, 0.1-15 weight % of oligosaccharide, 0.01-10 weight % of calcium and 0.001-5 weight % of vitamin were all dissolved to prepare syrup. The syrup was sterilized, cooled down, and mixed with the above culture solution, followed by stirring for homogenization. The resultant mixture was packed, resulting in the preparation of fermented milk. Flavor, physical property, and taste of the fermented milk product were tested, and the results were satisfactory.

Manufacturing Example 2

Preparation of Lactic Acid Bacteria Powder

*Lactobacillus gasseri* BNR17 of the invention was inoculated into MRS liquid medium at the concentration of $10^6$ cfu/ml, followed by pH-control fermentation at 37° C. for 18-24 hours. pH-control was performed by using 30 volume % NaOH as a neutralizing agent to pH 5.7±0.2. Upon completion of the culture, centrifugation was performed at 4° C. with 10,000×g to recover cells. A protectant supplemented with 5 weight % of skim milk, 2.5 weight % of whey, and 5 weight % of sucrose (for the total weight of the composition) was prepared. Equal amounts of the recovered cells and the protectant were mixed, followed by pulverization by using a freeze dryer. The produced *Lactobacillus gasseri* BNR17 dried powder contained over $1×10^{11}$ cfu/g live cells. The protectant can additionally include 10 weight % of trehalose, 10 weight % of maltodextrine and 7.5 weight % of lactose.

Manufacturing Example 3

Preparation of Lactic Acid Bacteria Products

Lactic acid bacteria products such as lactic acid bacteria foods and digestives were prepared from the lactic acid bacteria powder produced in Manufacturing Example 2. 10 weight % of oligosaccharide, 20 weight % of anhydrous glucose, 5 weight % of crystalline fructose, 2 weight % of vitamin C, 5 weight % of fruit powder flavor, 5 weight % of aloe, 15 weight % of dietary fiber, and 18 weight % of *Psyllium Husk* were added to 20 weight % of *Lactobacillus gasseri* BNR17 dried powder, and the mixture was packed in sticks or bottles. The live cells in the lactic acid bacteria product prepared thereby were more than $5×10^8$ cfu/g.

Manufacturing Example 4

Preparation of a Composition for Feed Additive

A composition for feed additive containing *Lactobacillus gasseri* BNR17 was prepared by the following compositions shown in Table 9.

TABLE 9

Component ratio of the composition for feed additive (weight %)

| | *Lactobacillus gasseri* BNR17 | Enzyme preparation | Nonpathogenic microorganism | Amino acid | Others |
|---|---|---|---|---|---|
| Manufacturing Example <4-1> | 100 | — | — | — | — |
| Manufacturing Example <4-2> | 90 | 10 | — | — | — |
| Manufacturing Example <4-3> | 80 | 10 | 10 | — | — |
| Manufacturing Example <4-4> | 70 | 10 | 10 | 10 | — |
| Manufacturing Example <4-5> | 60 | 15 | 15 | 8 | 2 |
| Manufacturing Example <4-6> | 50 | 20 | 15 | 8 | 2 |

The enzyme preparation used herein was a mixture of phytase, cellulase, xylase, maltase and invertase, and the nonpathogenic microorganism was *Aspergillus oryzae*.

INDUSTRIAL APPLICABILITY

As explained hereinbefore, the *Lactobacillus gasseri* BNR17 of the invention has wide growth temperature and pH ranges allowed. And, the strain of the invention not only has excellent acid resistance, bile acid resistance and enteric adsorption capacity but also strong antimicrobial activity against pathogenic microorganisms, in addition to weight gaining inhibitory effect. Therefore, the strain of the invention can be effectively used for the production of fermented milk and other fermented products and be very useful as an additive for animal feed as well.

SEQUENCE LISTING

Sequence listing is attached herewith.

---

What is claimed is:

1. A *Lactobacillus gasseri* BNR17 strain of a biologically pure culture deposited at Korean Collection for Type Culture of Korea Research Institute of Biotechnology and Bioscience under the Accession number of KCTC 10902BP.

2. The *Lactobacillus gasseri* BNR17 strain according to claim 1, wherein the strain contains 16S rRNA sequence represented by SEQ ID NO: 1.

3. A composition containing an effective dose of the *Lactobacillus gasseri* BNR17 of claim 1.

4. The composition according to claim 3, wherein the composition is selected from the group consisting of food, food additive, animal feed and animal feed additive.

5. The composition according to claim 4, wherein the animal feed additive contains at least one selected from the group consisting of other non-pathogenic microorganisms, enzymes and a mixture thereof.

6. A pharmaceutical composition comprising an effective dose of the *Lactobacillus gasseri* BNR17 of claim 1.

7. A culture solution of the *Lactobacillus gasseri* BNR17 of claim 1.

8. A method for inhibiting weight gain comprising administering to a subject an effective dose of the *Lactobacillus gasseri* BNR17 of claim 1.

* * * * *

SEQUENCE LISTING

<160> NUMBER OF SEQ ID NOS: 9

<210> SEQ ID NO 1
<211> LENGTH: 840
<212> TYPE: DNA
<213> ORGANISM: Lactobacillus gasseri BNR17
<220> FEATURE:
<221> NAME/KEY: misc_feature
<222> LOCATION: (181)..(181)
<223> OTHER INFORMATION: n is a, c, g, or t

<400> SEQUENCE: 1

```
gctgactcct ataaaggtta tcccaccggc tttgggtgtt acagactctc atggtgtgac      60
gggcggtgtg tacaaggccc gggaacgtat tcaccgcggc gtgctgatcc gcgattacta     120
gcgattccag cttcgtgtag gcgagttgca gcctacagtc cgaactgaga acggctttca     180
nagatccgct tgccttcgca ggttcgcttc tcgttgtacc gtccattgta gcacgtgtgt     240
agcccaggtc ataaggggca tgatgacttg acgtcatccc caccttcctc cggtttgtca     300
ccggcagtct cattagagtg cccaacttaa tgatggcaac taatgacaag ggttgcgctc     360
gttgcgggac ttaacccaac atctcacgac acgagctgac gacagccatg caccacctgt     420
ctcagcgtcc ccgaagggaa ctcctaatct cttaggtttg cactggatgt caagacctgg     480
taaggttctt cgcgttgctt cgaattaaac cacatgctcc accgcttgtg cgggcccccg     540
tcaattcctt tgagtttcaa ccttgcggtc gtactcccca ggcggagtgc ttaatgcgtt     600
agctgcagca ctgagaggcg gaaacctccc aacacttagc actcatcgtt tacggcatgg     660
actaccaggg tatctaatcc tgttcgctac ccatgctttc gagcctcagc gtcagttgca     720
gaccagagag ccgccttcgc cactggtgtt cttccatata tctacgcatt ccaccgctac     780
acatggagtt ccactctcct cttctgcact caagttcaac agtttctgat gcaattctcc     840
```

```
<210> SEQ ID NO 2
<211> LENGTH: 840
<212> TYPE: DNA
<213> ORGANISM: Lactobacillus gasseri KC26

<400> SEQUENCE: 2
gctgactcct ataaaggtta tcccaccggc tttgggtgtt acagactctc atggtgtgac      60
gggcggtgtg tacaaggccc gggaacgtat tcaccgcggc gtgctgatcc gcgattacta     120
gcgattccag cttcgtgtag gcgagttgca gcctacagtc cgaactgaga acggctttca     180
gagatccgct tgccttcgca ggttcgcttc tcgttgtacc gtccattgta gcacgtgtgt     240
agcccaggtc ataaggggca tgatgacttg acgtcatccc accttcctc cggtttgtca      300 ccggcagtct cattagagtg cccaacttaa tgatggcaac taatgacaag ggttgcgctc     360
gttgcgggac ttaacccaac atctcacgac acgagctgac gacagccatg caccacctgt     420
ctcagcgtcc ccgaagggaa ctcctaatct cttaggtttg cactggatgt caagacctgg     480
taaggttctt cgcgttgctt cgaattaaac cacatgctcc accgcttgtg cgggcccccg     540
tcaattcctt tgagtttcaa ccttgcggtc gtactcccca ggcggagtgc ttaatgcgtt     600
agctgcagca ctgagaggcg gaaacctccc aacacttagc actcatcgtt tacggcatgg     660
actaccaggg tatctaatcc tgttcgctac ccatgctttc gagcctcagc gtcagttgca     720
gaccagagag ccgccttcgc cactggtgtt cttccatata tctacgcatt ccaccgctac     780
acatggagtt ccactctcct cttctgcact caagttcaac agtttctgat gcaattctcc     840

<210> SEQ ID NO 3
<211> LENGTH: 20
<212> TYPE: DNA
<213> ORGANISM: Artificial Sequence
<220> FEATURE:
<223> OTHER INFORMATION: gaT-950 forward primer, specific to
      Lactobacillus gasseri

<400> SEQUENCE: 3
ggagtaggtg gagcgacagt                                                   20

<210> SEQ ID NO 4
<211> LENGTH: 20
<212> TYPE: DNA
<213> ORGANISM: Artificial Sequence
<220> FEATURE:
<223> OTHER INFORMATION: gaT-1075 reverse primer, specific to
      Lactobacillus gasseri

<400> SEQUENCE: 4
tccaccagta gctgccgtta                                                   20

<210> SEQ ID NO 5
<211> LENGTH: 110
<212> TYPE: DNA
<213> ORGANISM: Artificial Sequence
<220> FEATURE:
<223> OTHER INFORMATION: gassericin BNR17 gene originated from
      Lactobacillus gasseri BNR17

<400> SEQUENCE: 5
tgccgttacg ccagcccatg ctattggaac atagtgtgct ccaacagagc cacaagcagg       60 accgcaaaact gcatttccaa gagcccgtcc agcgactgtc gctccaccta                 110
```

```
<210> SEQ ID NO 6
<211> LENGTH: 110
<212> TYPE: DNA
<213> ORGANISM: Artificial Sequence
<220> FEATURE:
<223> OTHER INFORMATION: gassericin T gene originated from Lactobacillus
      gasseri and disclosed in NCBI Blast Search No. AB029612

<400> SEQUENCE: 6
tgccgttacg ccagcccatg ctattggaac atagtgtgct ccaacaaagc cacaagcagg      60
accgcaaact gcatttccaa gagcccatcc agcgactgtc gctccaccta               110

<210> SEQ ID NO 7
<211> LENGTH: 10
<212> TYPE: DNA
<213> ORGANISM: Artificial Sequence
<220> FEATURE:
<223> OTHER INFORMATION: primer p1, random sequence according to
      RAPD-PCR technique

<400> SEQUENCE: 7
agcagcgtgg                                                            10

<210> SEQ ID NO 8
<211> LENGTH: 10
<212> TYPE: DNA
<213> ORGANISM: Artificial Sequence
<220> FEATURE:
<223> OTHER INFORMATION: primer p2, random sequence according to
      RAPD-PCR technique

<400> SEQUENCE: 8
ggcatgacct                                                            10

<210> SEQ ID NO 9
<211> LENGTH: 10
<212> TYPE: DNA
<213> ORGANISM: Artificial Sequence
<220> FEATURE:
<223> OTHER INFORMATION: primer OPL5, random sequence according to
      RAPD-PCR technique

<400> SEQUENCE: 9
acgcaggcac                                                            10
```